(12) United States Patent
Scott et al.

(10) Patent No.: US 6,409,665 B1
(45) Date of Patent: Jun. 25, 2002

(54) APPARATUS FOR APPLYING IMPEDENCE MATCHING FLUID FOR ULTRASONIC IMAGING

(76) Inventors: Corey D. Scott, 1155 Northern Run, Stockbridge, GA (US) 30281; Arlene K. Patrick, 503 Abington Way, Atlanta, GA (US) 30328; Michael R. Hicks, 5283 Moat Peher Dr., Mableton, GA (US) 30126

( * ) Notice: Subject to any disclaimer, the term of this patent is extended or adjusted under 35 U.S.C. 154(b) by 23 days.

(21) Appl. No.: 09/585,164

(22) Filed: Jun. 1, 2000

(51) Int. Cl.[7] ................................................ A61B 8/00
(52) U.S. Cl. ...................................................... 600/437
(58) Field of Search ................................ 600/437, 443, 600/447, 459, 472; 73/296; 340/612–613

(56) References Cited

U.S. PATENT DOCUMENTS 4,282,880 A * 8/1981 Gardineer et al. .......... 600/443
4,844,080 A * 7/1989 Frass et al. ................. 600/437
5,836,880 A * 11/1998 Pratt ........................... 600/443

* cited by examiner

Primary Examiner—Francis J. Jaworski
(74) Attorney, Agent, or Firm—Eric R. Katz

(57) ABSTRACT

An apparatus is disclosed for applying impedance matching gel to an ultrasonic transducer head of an imaging device for application to a patient. The apparatus comprises: a reservoir for containing the impedance matching gel; a heater for heating the impedance matching gel in the reservoir to a predetermined temperature; a conduit for conveying the impedance matching gel from the reservoir to the ultrasonic transducer head; a pumping arrangement for supplying the heated impedance matching gel from the reservoir, via the conduit, to the ultrasonic transducer head for application to the patient; and a low gel sensing system for indicating when the amount of gel in the reservoir drops below a predetermined quantity to prevent overheating of the gel.

9 Claims, 4 Drawing Sheets

APPARATUS FOR APPLYING IMPEDENCE MATCHING FLUID FOR ULTRASONIC IMAGING

BACKGROUND

1. Field of the Invention

The present invention generally relates to an ultrasonic imaging method and apparatus for supplying impedance matching fluid to a body being imaged, and more particularly, to such a method and apparatus wherein the impedance matching fluid is supplied to the body being imaged in a manner that improves the efficiency of the ultrasonic imaging procedure as well as patient comfort.

2. Background Discussion

Ultrasonic imaging is used to perform non-invasive of imaging of an object, such as the body of a biological organism. Its non-ionizing character, moderate requirements in terms of signal processing and computation support, compactness and image quality all favor the use of ultrasound whenever conditions permit. With the exception of body areas which are subject to uncontrolled multiple reflections, such as, for example, the skull and areas which fundamentally possess poor sonic transmission characteristic, such as the lungs, most areas of the body have been successfully made the subject of ultrasonic diagnosis or screening.

Known ultrasonic imaging systems include arrangements using a hand-held scan head coupled by a cable to a processing and display unit. The scan head typically includes an array of ultrasonic transducers that transmit an acoustic signal in the form of ultrasonic energy into the region being imaged and receive reflected ultrasonic energy returning from the region. The transducers convert the reflected ultrasonic energy into electrical signals which are transferred over the cable to the processing unit which applies appropriate beam forming techniques, such as dynamic focusing, to combine the signals to generate an image of the region.

In order to propagate the acoustic signal and to minimize echoes at the point where the acoustic signal enters the object being imaged, a fluid having an acoustic impedance which substantially matches that of the object is typically situated between the ultrasonic transducer head of the imaging device and the object being imaged. When performing ultrasonic medical imaging, the impedance matching fluid utilized typically has an acoustic impedance which substantially matches that of human body tissue. Such impedance matching fluids generally have the consistency of a gel.

For ultrasonic imaging systems using a held-held transducer head, the impedance matching fluid or gel is typically applied to the patient's skin overlying the area of the body being imaged using a squeeze bottle dispenser that deposes a glob of the impedance matching gel on the skin of the patient. The hand-held transducer head is then placed in the glob of impedance matching fluid and used to spread the impedance matching as the transducer head is moved over the area being imaged. More gel must be applied after all the gel has been spread and/or as the gel dries out during the imaging procedure. Reapplication of the gel may be required as many as thirty times during a given ultrasonic imaging procedure.

As a result, frequent re-application of the impedance matching gel is required during the imaging procedure thereby reducing the efficiency of process and increasing the time that is required to complete the examination as well as patient discomfort. In addition, the gel in the squeeze bottle dispenser typically has a temperature at or near the ambient room temperature. The room temperature of the gel coupled with the evaporation of the gel on the skin makes the gel feel cold to the patient, thereby further increasing patient discomfort.

SUMMARY OF THE INVENTION

Accordingly, it is an object of the present invention provide a method and apparatus for applying an impedance matching fluid to the body of a patient having an ultrasonic imaging procedure in a manner that improves the efficiency of the ultrasonic imaging procedure as well as patient comfort.

Another object of the present invention is to solve the problem of constantly having to stop and re-apply the impedance matching gel to the patient during the ultrasound imaging procedure.

Still a further object of the present invention is to increase patient comfort by warming the gel that is applied.

An advantageous feature of the present invention is the ability to easily retro-fit the apparatus to existing ultrasound imaging devices.

Another advantageous feature of the apparatus of the present invention is that it can be used with ultrasonic scan heads having different shapes and configurations.

These and other objects, advantages and features of the present invention are achieved, according to one embodiment thereof, by an apparatus for heating and supplying an impedance matching fluid in gel form to the body of a patient having an ultrasonic imaging procedure, wherein the apparatus comprises: 1) a reservoir of containing the impedance matching gel; 2) a heater, inserted into the reservoir, for warming the gel, the heater having a thermostat for setting the temperature of the gel; 3) a pumping arrangement for supplying the heated gel, via a conduit, to the hand-held transducer head of the ultrasonic imaging device, the pumping arrangement having a vacuum activated on/off switch located for easy access at the transducer head; and 4) a low gel sensing system for providing an indication when the gel in the reservoir drops to a predetermined quantity to prevent overheating.

According to a further embodiment of the present invention, the low gel sensing system comprises a warning system including an arrangement for sensing the weight of the reservoir such that a series of switches: a) illuminate a green light when sufficient gel is in the reservoir to prevent overheating and b) active a red light and a piezoelectric alarm when the weight of the gel containing reservoir drops below a predetermined weight.

The present invention also includes a method of applying an impedance matching fluid to a patient having an ultrasonic imaging procedure which, according to one embodiment thereof comprises the steps of: heating the impedance matching fluid to a given temperature; and applying the heated impedance matching fluid to the patient.

According to a further embodiment of the present invention, there is provided a method of applying an impedance matching fluid to a patient having an ultrasonic imaging procedure using a hand-held ultrasonic transducer of an ultrasonic imaging device, the method comprising the steps of: heating impedance matching fluid contained in a reservoir to a given temperature; providing a supply of heated impedance matching fluid from the reservoir to the hand-held ultrasonic transducer; and applying the heated impedance matching fluid to the patient from the hand-held ultrasonic transducer. This method can further comprise the step of: generating a low impedance matching fluid indication when the impedance matching fluid in the reservoir drops to a predetermined quantity to advise the operator that more gel needs to be added to the reservoir and/or to prevent overheating of the impedance matching fluid by the heater due to the small quantity of gel in the reservoir.

DETAILED DESCRIPTION OF THE PREFERRED EMBODIMENTS

Figure 1:
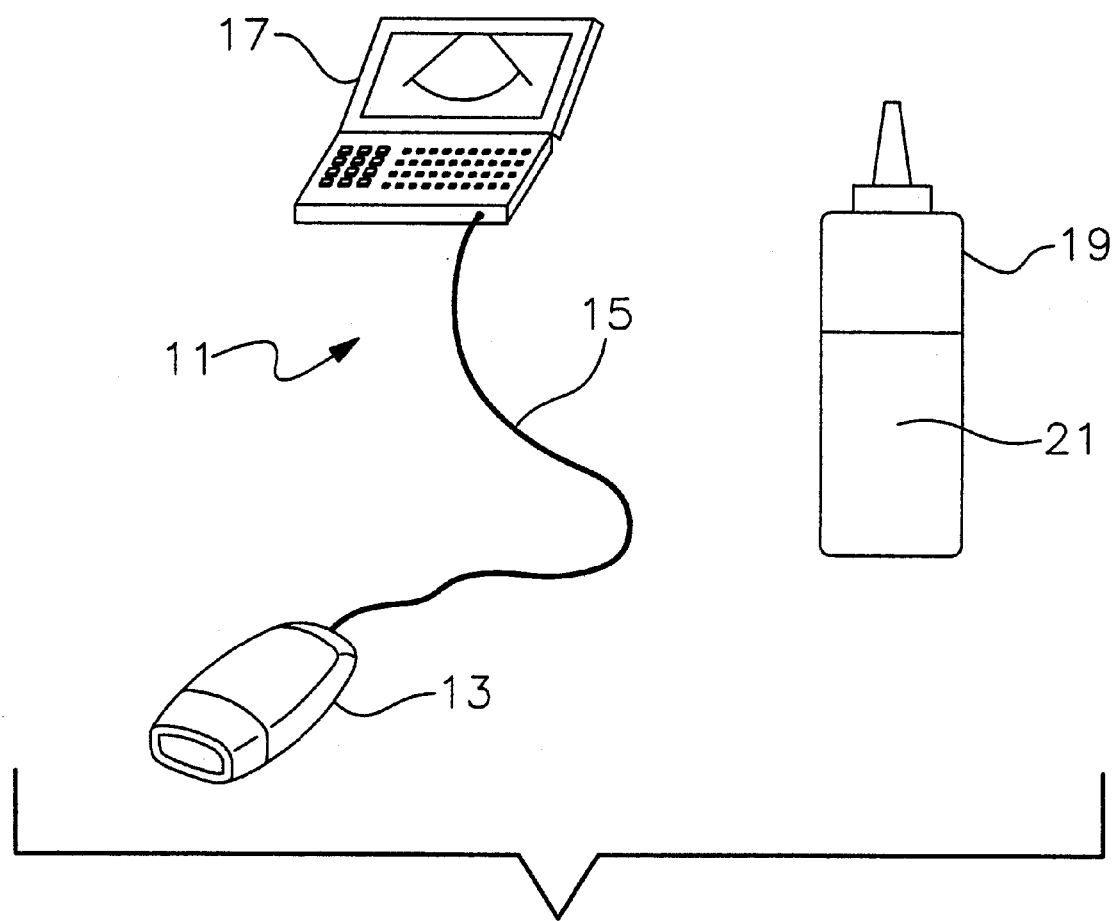
FIG. 1 illustrates a prior art ultrasonic imaging system that uses a hand-held scan head.

Referring to FIG. 1, a prior art ultrasonic imaging system, generally indicated at 11, is illustrated that includes a hand-held scan head 13 coupled by a cable 15 to a processing and display unit 17. It should be noted that the hand-held scan head 13 illustrated in FIG. 1 is shown by way of example only. The shape and configuration of the scan head 13 varies according to the requirements of the imaging procedure being performed. For example, a cardiac scan head is pencil thin whereas one used to image the stomach area is much wider and bigger. Also shown in FIG. 1 is a squeeze bottle, dispensing unit 19 containing impedance matching fluid or gel 21 that is typically applied to the patient's skin overlying the area of the body being imaged by the system 11. As previously described, the squeeze bottle, dispensing unit 19 is used to depose a glob of the impedance matching gel 21 on the skin of the patient (not shown).

In operation, the hand-held transducer head 13 is placed in the glob of impedance matching gel 21 which is then spread over the patient's skin as the transducer head is moved over the area being imaged. More gel 21 must be applied after all the gel 21 has been spread and/or as the gel 21 dries out during the imaging procedure. Reapplication of the gel 21 may be required as many as thirty times during a given ultrasonic imaging procedure. It should also be noted that ultrasonic imaging procedures are typically performed in dim light so that the medical technicians can clearly see the image on the display unit 17.

Figure 2:
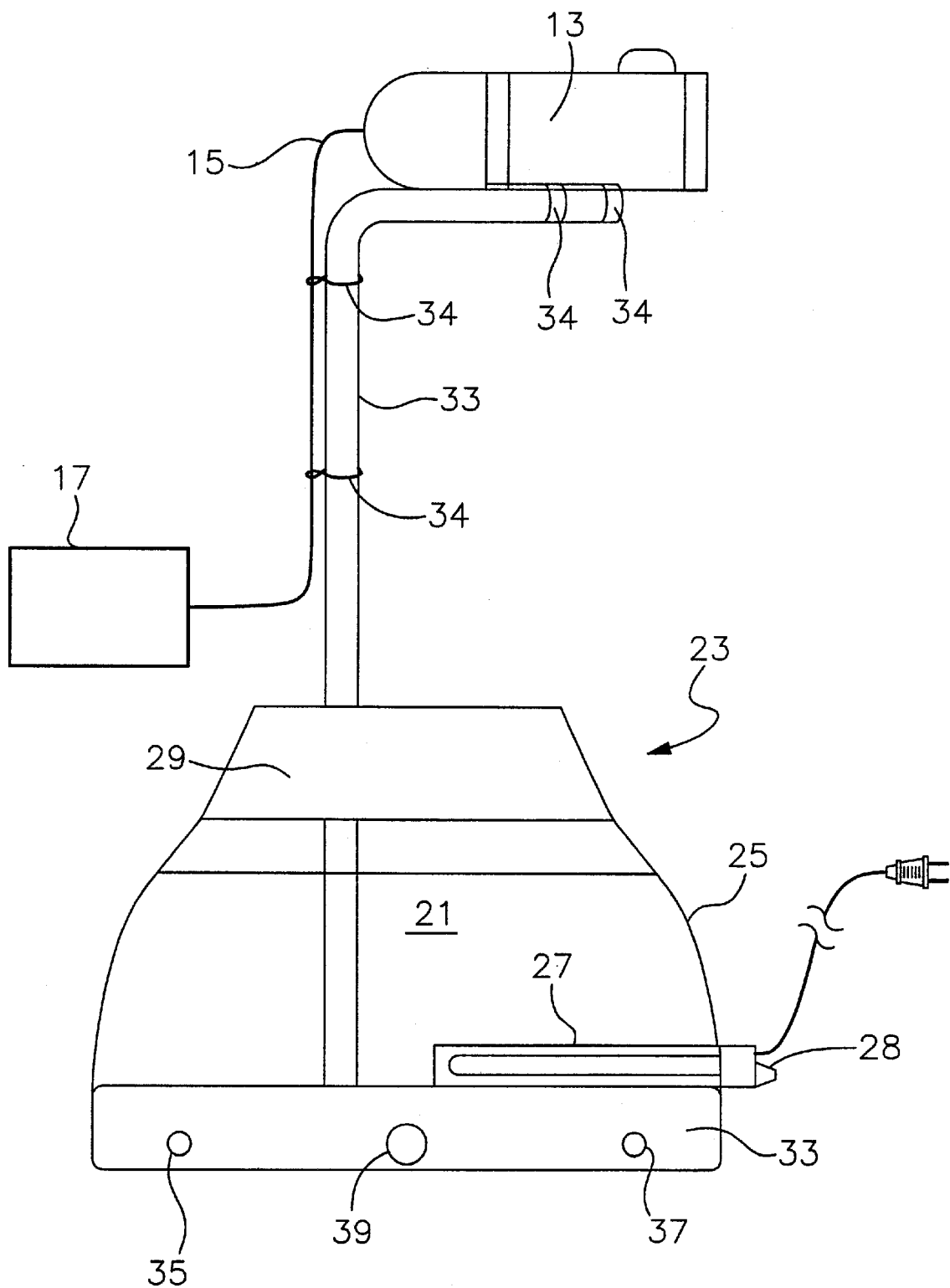
FIG. 2 illustrates one embodiment of the apparatus of the present invention.

FIG. 2 schematically illustrates one embodiment of an apparatus, generally indicated at 23, for applying the impedance matching gel 21 to the body of the patient having an ultrasonic imaging procedure. It should be noted that the apparatus 23 and its elements depicted by FIG. 2 are not to scale and the representation provided thereby is illustrative only. The apparatus 23 is particularly adapted for use with ultrasonic imaging systems using a hand-held ultrasonic-transducer such as shown in FIG. 1. As will become apparent as the description of the present invention proceeds, he apparatus 23 is easily retro-fitted to existing ultrasonic imaging systems regardless of the configuration and/or size and shape of the scan head.

Referring to FIG. 2, the apparatus 23 includes a reservoir 25 for containing the impedance matching gel 21. Inserted into the reservoir is a heater 27 for warming the gel 21. The heater 27 comprises, for example, an glass enclosed electric heater having a settable thermostat controlled, for example, by a knob 28 or the like. The heater 27, which has a plug for insertion into a typical electrical outlet, comprises, for example, an aquarium heater such as used to keep the temperature of water in a tropic fish tank at the proper temperature. The heater 27 is installed into the reservoir 25 by cutting a hole in a wall of the reservoir 25, inserting the heater 27 into the interior of the reservoir 25 so that the thermostatic control knob 28 is positioned at the exterior of the reservoir 25 and then the space between the hole and the heater 27 is sealed, for example, with caulk or the like.

A pumping arrangement 29, controlled at the hand-held transducer head 13 by switch 31, is provided for supplying the heated gel 21, via a flexible conduit 33, to the hand-held transducer head 13 of the ultrasonic imaging systems 11. The conduit 33 comprises, for example, flexible tubing or hose having an internal diameter of between about one to a quarter of an inch. The conduit 33 is positioned parallel to the cable 15 connecting the scan head 13 to the processing and imaging unit 17 of the ultrasonic imaging system 11, for example, by attaching the conduit 33 to the cable 15 using clips or brackets 34 or the like. The conduit 33 is similarly attached to the scan head 13 using, for example, by a clip or bracket 34.

The pumping arrangement 29 comprises, for example, the same pumping arrangement employed by Wagner Spray Tech Corporation, having offices at 1770 Fernbrook Lane, Minneapolis, Minn. 55447, in its hand-held paint sprayers or High Volume Low Pressure (HVLP) sprayers. The Wagner pumping arrangements are preferred because latex paints and other similar liquid coatings have a viscosity and consistency similar to that of the gel 21. In addition, such pumping arrangements are sold commercially and available to the public. The switch 31 schematically illustrated in FIG. 2 comprises, for example, a vacuum switching arrangement such as used to turn on and off the spray of paint or coating materials from the Wagner hand-held paint sprayers noted above.

The apparatus 23 is actually much smaller in relation to the imaging system 11 than shown by FIG. 2 and therefore can be position, out of the way, on a tray (not shown) at or under the processing and imaging unit 17. Alternatively, the apparatus can be positioned on a cart having wheels (not shown) and moved independently of the ultrasonic imaging systems 11. In either case, the apparatus 23 can be fitted to a particular ultrasonic imaging system 11 then removed and fitted to a different ultrasonic imaging system at a different location quite easily.

According to another embodiment of the present invention, the apparatus 23 further includes a low gel sensing system 33 for indicating when the gel 21 in the reservoir 25 drops to a predetermined quantity. This is important to prevent overheating of the gel 21 when the quantity of impedance matching gel 21 in the reservoir 25 gets too low. The sensing system 33, as illustrated by FIG. 2, is configured as a warning system and includes, as will be more fully described hereinafter with particular reference to FIG. 3, an arrangement for sensing the total weight of the reservoir 25 such that a series of switches: a) illuminate a green light 35 when sufficient gel 21 is in the reservoir to prevent overheating and b) active a red light 37 and/or an auditory alarm 39, such as a piezoelectric device, when the weight of the gel containing reservoir 25 drops below a predetermined weight.

Figure 3:
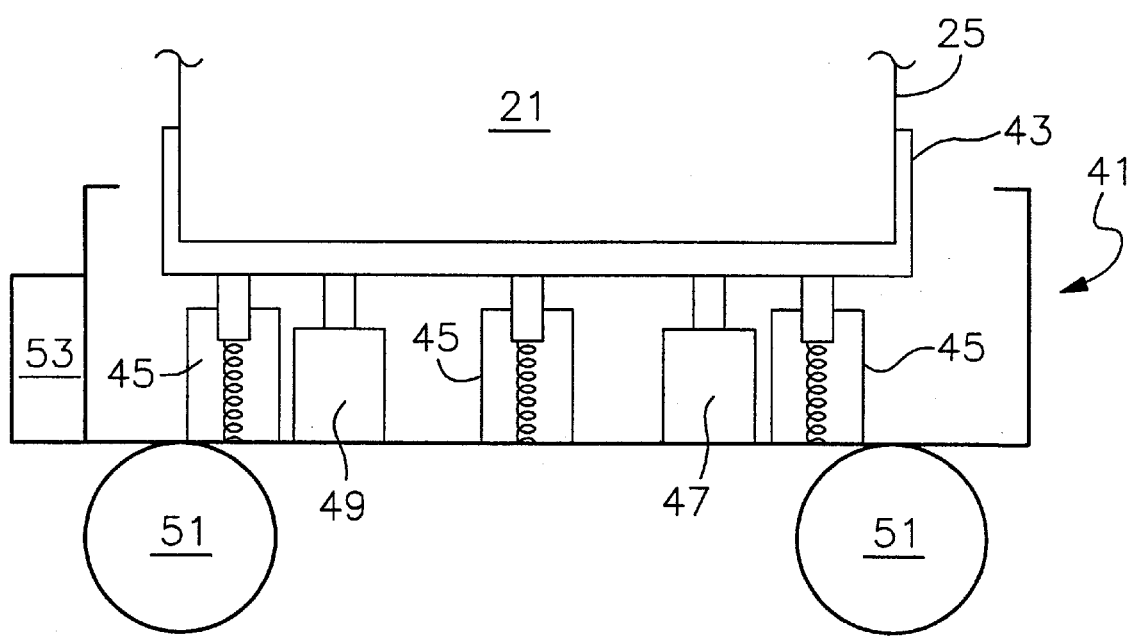
FIG. 3 is a sectional, side view of one embodiment of a low gel sensing system for providing an indication when the impedance matching gel drops to a predetermined quantity.

Referring to FIG. 3, a sectional side view of one embodiment of the low gel sensing system 33 is shown. The sensing system 33 is powered by, for example, a dc power supply provided by an ac-to-dc converter (not shown) which is plugged into a conventional ac electrical outlet. The support 41 has, for example, wheels or rollers 51 so that the entire apparatus 23 is mobile. In addition, an electrical power plug strip, such as, for example, a surge protector 53, is mounted on the side of the support 41 so that an operating technician can plug the pumping arrangement 29, heater 27 and ac-to-dc converted all into the surge protector 53.

The system 33 comprises a support, generally indicated at 41, having a tray or shelf 43 on which the reservoir 25 of the apparatus 23 is placed. The tray 43 is mounted on the support 41 using a plurality of spring-biased members 45. Also included are a pair of contact switches 47, 49. Contact switch 47, for example, is adapted to connect green light 35 to the dc power supply when switch 47 is depressed and contact switch 49, for example, is adapted to connect red light 37 and/or audio alarm 39 to the do power supply when switch 49 is released.

The springs of the members 45 are calibrated such that when the weight of the gel 21 in the reservoir 25 is greater than a predetermined value, the tray 43 pushes downward against the spring-bias of the members 45 so as to depress contact switch 47. Since contact switch 47 is closed, the green light 35 is connected to the dc power source (not shown) and illuminated thereby indicating to the operating technician that sufficient gel is in the reservoir 25. As the gel 21 is pumped from the reservoir 25, the force exerted against the members 45 decreases causing the support 41 to move upward until switch 49 is released. Since upon release, contact switch 49 is closed, the red light 37 and/or audio alarm 39 are connected to the do power source and activated to provide an indication that the gel 21 in the reservoir 25 is low and needs to be replenished.

Figure 4:
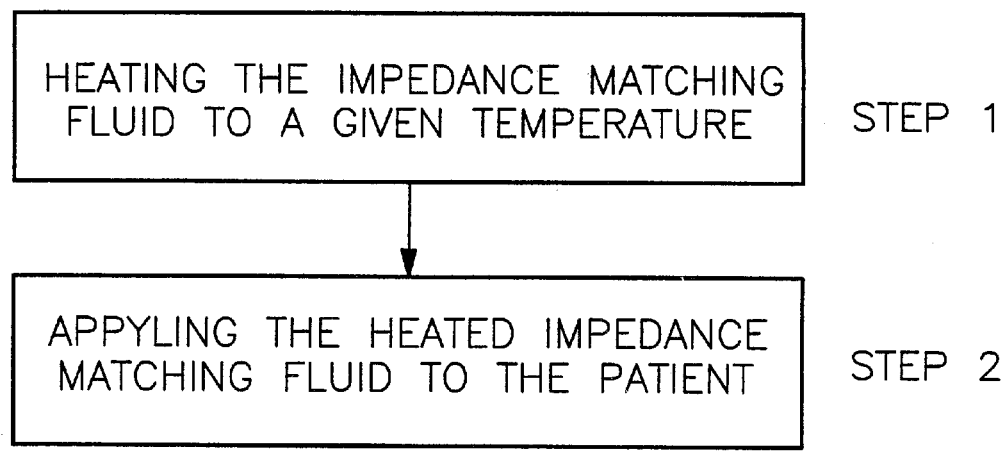
FIG. 4 is a block diagram illustrating one embodiment of the method of the present invention.

Referring to FIG. 4, one embodiment of a method of applying an impedance matching fluid to a patient having an ultrasonic imaging procedure is illustrated. The method comprises the steps of: heating the impedance matching fluid to a given temperature; and applying the heated impedance matching fluid to the patient. The temperature to which the impedance matching fluid is heated is a temperature that feels comfortable to the individual patient. As a result the exact temperature of the fluid may vary from patient to patient.

Figure 5:
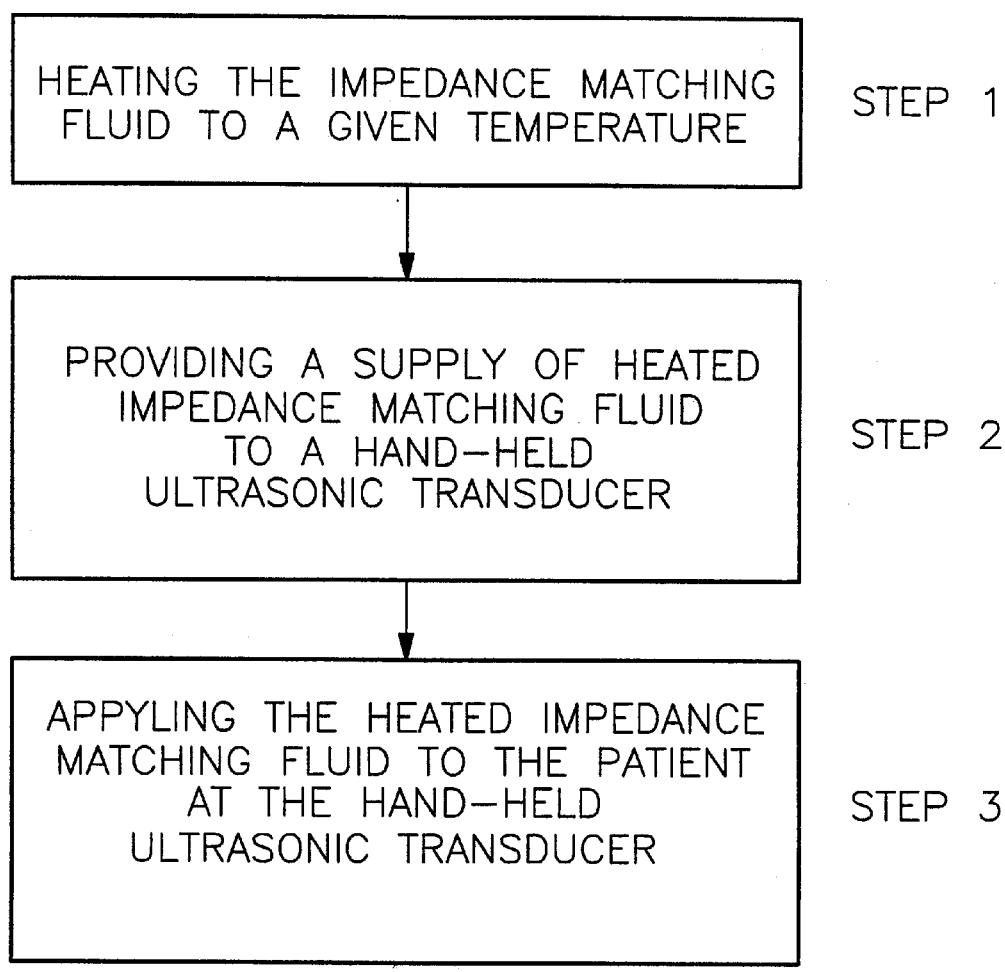
FIG. 5 is a block diagram illustrating a further embodiment of the method of the present invention.

Referring to FIG. 5, a further embodiment of the method of applying an impedance matching fluid to a patient having an ultrasonic imaging procedure is illustrated. This embodiment is particularly adapted for use with ultrasonic imaging procedures using a hand-held ultrasonic transducer and comprises the steps of heating impedance matching fluid to a given temperature; providing a supply of heated impedance matching fluid to the hand-held ultrasonic transducer; and applying the heated impedance matching fluid to the patient at the hand-held ultrasonic transducer.

While the invention has been described as having a preferred design, the present invention can be further modified within the spirit and scope of this disclosure. This application is therefore intended to cover any variations, uses or adaptations of the invention using its general principles. Further, this application is intended to cover departures from the present invention as come within known or customary practice in the art to which this invention pertains and which fall within the scope of the appended claims.

What is claimed is:

1. An apparatus for applying impedance matching gel to an ultrasonic transducer head of an imaging device for application to a patient, the apparatus comprising:
    a reservoir for containing the impedance matching gel;
    a heater for heating the impedance matching gel in the reservoir to a predetermined temperature;
    a conduit for conveying the impedance matching gel from the reservoir to the ultrasonic transducer head;
    a pumping arrangement for supplying the heated impedance matching gel from the reservoir, via the conduit, to the ultrasonic transducer head for application to the patient; and
    a low gel sensing system for indicating when an amount of gel in the reservoir drops below a predetermined quantity to prevent overheating of the gel.

2. An apparatus according to claim 1, wherein the low gel sensing system comprises:
    an arrangement for sensing the weight of the gel-containing reservoir; and
    an alarm activated when the arrangement for sensing the weight of the gel-containing reservoir indicates the weight of the gel-containing reservoir has dropped below a predetermined weight.

3. An apparatus according to claim 2, wherein the low gel sensing system further comprises a green light which is illuminated when the amount of gel in the reservoir is sufficient to prevent overheating.

4. An apparatus according to claim 2, wherein the arrangement for sensing the weight of the gel-containing reservoir comprises:
    a support;
    at least one spring-biased member for supporting the reservoir at the support; and
    a contact switch for activating the alarm when the contact switch is released, the contact switching being depressed when the weight of the reservoir on the tray is greater than the predetermined weight;
    wherein, the spring-biased member is calibrated so that as the weight of the gel in the reservoir drops below the predetermined weight and the force exerted against the spring-biased member decreases, the reservoir moves upward until the contact switch is released thereby activating the alarm.

5. An apparatus according to claim 4, wherein the alarm provides a visual indication when activated.

6. An apparatus according to claim 4, wherein the alarm provides an auditory indication when activated.

7. An apparatus according to claims 4, wherein the alarm provides both an auditory and a visual indication when activated.

8. An apparatus according to claim 4, wherein the low gel sensing system further comprises a green light which is illuminated when there is sufficient gel in the reservoir to prevent overheating.

9. An apparatus according to claim 1, further including a thermostat for controlling the heater so that the impedance matching gel is heated to a temperature that feels comfortable to the patient.

* * * * *